(12) United States Patent
Hendrix et al.

(10) Patent No.: US 8,486,124 B2
(45) Date of Patent: Jul. 16, 2013

(54) CONTROLLED PROTOCOL TIMER

(75) Inventors: Steven Hendrix, Sagamore Hills, OH (US); Kenneth Oif, Beachwood, OH (US); Michael Kaufman, Beachwood, OH (US)

(73) Assignee: National Biological Corporation, Beachwood, OH (US)

( * ) Notice: Subject to any disclaimer, the term of this patent is extended or adjusted under 35 U.S.C. 154(b) by 1643 days.

(21) Appl. No.: 11/940,852

(22) Filed: Nov. 15, 2007

(65) Prior Publication Data

US 2008/0125834 A1    May 29, 2008

Related U.S. Application Data

(60) Provisional application No. 60/859,363, filed on Nov. 15, 2006.

(51) Int. Cl.
*A61N 5/06* (2006.01)

(52) U.S. Cl.
USPC .......................................................... 607/88

(58) Field of Classification Search
USPC .................................. 607/88; 700/306, 286
See application file for complete search history.

(56) References Cited

U.S. PATENT DOCUMENTS

| | | | | |
|---|---|---|---|---|
| 4,428,050 A * | 1/1984 | Pellegrino et al. | ............ | 250/372 |
| 4,835,749 A * | 5/1989 | Welton | .............................. | 368/10 |
| 5,363,347 A * | 11/1994 | Nguyen | ........................... | 368/10 |
| 5,601,619 A | 2/1997 | Drechsler | | |
| 5,871,520 A * | 2/1999 | Nguyen | ........................... | 607/88 |
| 6,345,215 B1 | 2/2002 | Drechsler | | |
| 6,447,537 B1 | 9/2002 | Hartman | | |
| 6,749,623 B1 | 6/2004 | Hsi et al. | | |
| 6,866,678 B2 | 3/2005 | Shenderova et al. | | |
| 7,931,028 B2 * | 4/2011 | Jay | ................................. | 128/898 |
| 2006/0206171 A1 | 9/2006 | Gertner et al. | | |

OTHER PUBLICATIONS

International Search Report issued May 20, 2008.

* cited by examiner

*Primary Examiner* — Ralph Lewis
(74) *Attorney, Agent, or Firm* — Ulmer & Berne LLP (57) ABSTRACT

A phototherapy treatment dispensing device provides therapeutic light emissions treatments. The device provides additional means for controlling a patient's exposure to those treatments through a controlled protocol timer. The controlled protocol timer can provide for incremental exposure increases; monitors patient compliance with a treatment regimen; and reminds the patient when a treatment will soon be overdue.

27 Claims, 8 Drawing Sheets

CONTROLLED PROTOCOL TIMER

CROSS-REFERENCE TO RELATED APPLICATIONS

This application claims priority to U.S. Provisional Patent Application No. 60/859,363, filed on Nov. 15, 2006. The provisional application is hereby fully incorporated herein by reference.

BACKGROUND

The present disclosure relates generally to controls for phototherapeutic devices useful for ultraviolet light phototherapy. Methods of making and using such controls and/or devices are also disclosed.

Phototherapy relates to the treatment of disease, such as skin conditions including psoriasis, acne, eczema, vitiligo, and mycosis fungoides, by exposure to light, especially by various concentrated light rays such as long-wave or short-wave ultraviolet light. The treatment may be alone or in combination with a sensitizer which sensitizes the skin to light.

In particular, ultraviolet light ("UV light," radiation in the region of the electromagnetic spectrum including wavelengths from 100 to 4000 angstroms) has been used for over 30 years in a clinical setting for treating severe skin diseases, such as psoriasis and vitiligo. The treatment regimen is called phototherapy.

In a clinical setting, a physician, nurse or phototherapy technician is responsible for ensuring that a patient receives the correct treatment protocol. The protocol comprises a series of light exposure sessions including the duration of exposure for each session and the frequency of sessions (i.e, the interval between sessions).

In the 1990s, National Biological Corporation of Twinsburg, Ohio began offering a home-based phototherapy medical device that was approved by the Food and Drug Administration for sale in the United States. One concern of such a device was that unsupervised usage of the device by patients to administer ultraviolet light sessions could result in patients burning themselves. This concern was ameliorated by the provision of a prescription-controlled timing device, known as a controlled prescription timer, in phototherapy medical devices offered under the brand name PANOSOL II.

In the PANOSOL II, the controlled prescription timer was preprogrammed with a fixed number of sessions for the patient. When the fixed number of sessions was exhausted, the patient could obtain additional sessions by contacting their physician. The physician would authorize the additional sessions by providing a code number that the patient would enter into the keypad of their home phototherapy device. For additional information, see U.S. Pat. Nos. 5,604,619 and 6,345,215, the entire contents of both patents being fully incorporated herein by reference. National Biological Corporation has sold over 15,000 home phototherapy devices in the 10-year period up to 2006.

However, more people could benefit from home-based ultraviolet light phototherapy. For example, an estimated 2-3% of the population has a severe version of the skin disease psoriasis. Psoriasis is a common skin disease characterized by thickened patches of inflamed, red skin, often covered by silvery scales. The exact cause of psoriasis is not known. It affects men and women relatively equally. The underlying abnormality in psoriasis is that new skin cells are produced much faster than normal, but the rate at which cells are shed remains unchanged. Consequently, the live cells build up and form thickened patches covered with dead, flaky skin.

Phototherapy is generally considered the safest, most effective, and least expensive option for sufferers of severe psoriasis. With the US population approaching 300 million, 9 million potential patients could benefit from a home phototherapy device.

Some prescribing dermatologists have embraced the control offered by the controlled prescription timer and prescribed home phototherapy. However, a controller that provides additional control over patients' usage of the phototherapy device is beneficial.

Accordingly, there is a need for devices that provide additional control over patients' usage of a home-based phototherapy device.

BRIEF DESCRIPTION

Disclosed herein, in various exemplary embodiments, are treatment dispensing devices that include additional means for controlling usage of the device. The device provides a controlled protocol timer that embodies the instructions for using the device. The controlled protocol timer can provide for incremental exposure increases; monitors patient compliance with a treatment regimen; and reminds the patient when a treatment will soon be overdue. Methods and processes of making and using such devices are also disclosed. The controlled protocol timer is especially useful in medical devices.

In embodiments, a light treatment dispensing device comprises:
  a generator including a light emission device for emitting a therapeutic light emissions treatment; and
  a controller configured to control the generator, the controller including:
    (A) an engine that contains a prescribed protocol, each protocol comprising (i) a prescribed number of sessions, (ii) a prescribed session frequency, (iii) a prescribed number of treatments per session, and (iv) a prescribed duration for each treatment;
    (B) a treatment limiter configured to limit a number of therapeutic light emissions treatments according to the prescribed number of sessions and the prescribed number of treatments per session of the protocol;
    (C) a frequency limiter configured to limit a frequency at which therapeutic light emissions treatments are dispensed according to the prescribed session frequency of the protocol;
    (D) a duration limiter configured to limit a duration of a particular treatment to the prescribed duration for the particular treatment according to the protocol;
    (E) a timer configured to time a total actual duration of therapeutic light emissions treatments in a first period of time; and
    (F) a calculator for calculating a permitted increase in a total duration of therapeutic light emissions treatments in a second period of time based on the total actual duration of therapeutic light emissions treatments in the first period of time.

The controller may further include an input means for entering a passcode corresponding to a desired prescription, wherein the engine is configured to convert the passcode to the prescribed protocol.

The permitted increase may be based on a percentage of the total actual duration of therapeutic light emissions treatments in the first period of time.

The first and second periods of time may bother be from 2 hours to 96 hours.

The timer may further time an actual duration and a beginning time of a therapeutic light emissions treatment; and the device may further comprise a recorder for recording the beginning time and the actual duration of the therapeutic light emissions treatment. The device can also include a transmitter for transmitting the recorded beginning time and actual duration of the therapeutic light emissions treatment to a third party.

The device may further comprise: a comparator for comparing (i) an elapsed time beginning after the end of a particular session and (ii) the prescribed session frequency; and an alarm for generating an alert when the elapsed time differs from the prescribed session frequency by a specified amount.

In other embodiments, a light treatment dispensing device comprises:
- a generator including a light emission device for emitting a therapeutic light emissions treatment; and
- a controller configured to control the generator, the controller including:
  - (A) an engine that contains a prescribed protocol, each protocol comprising (i) a prescribed number of sessions, (ii) a prescribed session frequency, (iii) a prescribed number of treatments per session, and (iv) a prescribed duration for each treatment;
  - (B) a limiter configured to limit (i) a number of therapeutic light emissions treatments according to the prescribed number of sessions and the prescribed number of treatments per session of the protocol, (ii) a frequency at which therapeutic light emissions treatments are dispensed according to the prescribed session frequency of the protocol, and (iii) a duration of a particular treatment to the prescribed duration for the particular treatment according to the protocol;
  - (C) a timer configured to time a total actual duration of therapeutic light emissions treatments in a first period of time; and
  - (D) a calculator for calculating a permitted decrease in a session frequency based on the total actual duration of therapeutic light emissions treatments in the first period of time.

The controller may further include an input means for entering a passcode corresponding to a desired treatment schedule, wherein the engine is configured to convert the passcode to the prescribed protocol.

In still other embodiments, a phototherapy treatment dispensing device comprises:
- a generator for generating a therapeutic light emissions treatment;
- a controller configured to control the generator, the controller including:
  - (A) an engine that contains a prescribed protocol, each protocol comprising (i) a prescribed number of sessions, (ii) a prescribed session frequency, (iii) a prescribed number of treatments per session, and (iv) a prescribed duration for each treatment;
  - (B) a treatment limiter configured to limit a number of therapeutic light emissions treatments according to the prescribed number of sessions and the prescribed number of treatments per session of the protocol;
  - (C) a frequency limiter configured to limit a frequency at which therapeutic light emissions treatments are dispensed according to the prescribed session frequency of the protocol;
  - (D) a duration limiter configured to limit a duration of a particular treatment to the prescribed duration for the particular treatment according to the protocol; and
  - (E) a timer for timing an actual duration of the therapeutic light emissions treatment and a beginning time of the therapeutic light emissions treatment;
- a recorder for recording the beginning time and the actual duration of the therapeutic light emissions treatment; and
- a transmitter for transmitting the recorded beginning time and actual duration of the therapeutic light emissions treatment to a third party.

The controller may further include an input means for entering a passcode corresponding to a desired treatment schedule, wherein the engine is configured to convert the passcode to the prescribed protocol.

The transmitter may be selected from the group consisting of a removable medium, a wired connection, a wireless connection utilizing a sound, ultrasound, radio, microwave, infrared, or optical transmission medium, or a human-readable display that requires an authentication code.

The timer may further time a total actual duration of therapeutic light emissions treatments in a first period of time; and the device may further comprise a calculator for calculating a permitted increase in the total duration of therapeutic light emissions treatments in a second period of time based on the total actual duration of therapeutic light emissions treatments in the first period of time.

The device may further comprise: a comparator for comparing (i) an elapsed time beginning after the end of a particular session and (ii) the prescribed session frequency; and an alarm for generating an alert when the elapsed time differs from the prescribed session frequency by a specified amount.

In yet other embodiments, a phototherapy treatment dispensing device for providing a therapeutic radiation treatment is disclosed, the device including a controller configured to perform a method comprising:
- providing a prescribed protocol, the protocol comprising (i) a prescribed number of sessions, (ii) a prescribed session frequency, (iii) a prescribed number of treatments per session, and (iv) a prescribed duration for each treatment;
- timing an elapsed time beginning after the end of a particular session;
- comparing the elapsed time to the prescribed session frequency; and
- generating an alert when the elapsed time differs from the prescribed session frequency by a specified amount.

The specified amount may be a percentage of the prescribed session frequency.

In other embodiments, a treatment dispensing device comprises a treatment dispenser and a controller, the controller including:
- (A) an engine that contains a prescribed protocol, each protocol comprising (i) a prescribed number of sessions, (ii) a prescribed session frequency, (iii) a prescribed number of treatments per session, and (iv) a prescribed duration for each treatment;
- (B) a treatment limiter configured to limit a number of dispensed treatments according to the prescribed number of sessions and the prescribed number of treatments per session of the protocol;
- (C) a frequency limiter configured to limit a frequency at which treatments are dispensed according to the prescribed session frequency of the protocol; and (D) a duration limiter configured to limit a duration of a particular treatment to the prescribed duration for the particular treatment according to the protocol.

The controller may further include an input means for entering a passcode corresponding to a desired treatment schedule, wherein the engine is configured to convert the passcode to the prescribed protocol.

A method for controlling the exposure of a patient using a light treatment dispensing device is also disclosed, comprising:
 providing a light treatment device capable of producing a therapeutic light emissions treatment and containing a prescribed protocol, each protocol comprising (i) a prescribed number of sessions, (ii) a prescribed session frequency, (iii) a prescribed number of treatments per session, and (iv) a prescribed duration for each treatment;
 producing a therapeutic light emissions treatment;
 recording a beginning time and an actual duration of the therapeutic light emissions treatment; and
 transmitting the recorded beginning time and actual duration of the therapeutic light emissions treatment to a third party.

In some embodiments, multiple therapeutic light emissions treatments are produced; the beginning time and actual duration of each treatment is recorded, and the recorded beginning time and actual duration of the multiple treatments are simultaneously transmitted to the third party.

Another method for controlling the exposure of a patient using a phototherapy treatment dispensing device comprises:
 providing a phototherapy treatment device capable of (A) producing a therapeutic light emissions treatment and (B) containing a prescribed protocol, each protocol comprising a first session, a second session, and a session interval;
 comparing (i) an elapsed time beginning after the end of the first session and (ii) the session interval; and
 generating an alarm when the elapsed time differs from the session interval by a specified amount.

Other methods for controlling the usage of a treatment dispensing device, comprise:
 entering a passcode corresponding to a particular profile;
 providing a treatment device capable of dispensing a treatment and generating a prescribed protocol from the passcode, each protocol comprising (i) a prescribed number of sessions, (ii) a prescribed session frequency, and (iii) a prescribed duration for each session;
 limiting the number of sessions to the prescribed number of sessions of the protocol;
 limiting the frequency between successive sessions to the prescribed session frequency of the protocol; and
 limiting the duration of a particular session to the prescribed duration for the particular session according to the protocol.

The method may further comprise:
 measuring a total actual duration of treatments dispensed in a first period of time; and
 determining a permitted increase in a total duration of treatments allowed in a second period of time based on the total actual duration of treatments dispensed in the first period of time.

Alternatively, the method may further comprise:
 recording a beginning time and an actual duration of each treatment; and
 transmitting the recorded beginning time and actual duration of each treatment to a third party.

Other methods may further comprise:
 recording the ending time of a treatment and an elapsed time since the ending time; and
 generating an alarm when the elapsed time differs from the prescribed session frequency of the protocol.

These and other non-limiting aspects and/or objects of the development are more particularly disclosed below.

BRIEF DESCRIPTION OF THE DRAWINGS

The following is a brief description of the drawings, which are presented for the purposes of illustrating the development disclosed herein and not for the purposes of limiting the same.

DETAILED DESCRIPTION

A more complete understanding of the processes and apparatuses disclosed herein can be obtained by reference to the accompanying drawings. These Figures are merely schematic representations based on convenience and the ease of demonstrating the present development, and are, therefore, not intended to indicate relative size and dimensions of the phototherapeutic devices or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to component of like function.

The present disclosure relates to treatment dispensing devices that have imbedded in them a controlled protocol timer. The controlled protocol timer imbeds in the treatment dispensing device a full profile for the usage of that device. Controlled protocol timers may be useful in any sort of device. In particular, the disclosure relates to medical devices, light treatment dispensing devices, and phototherapy treatment dispensing devices where the controlled protocol timer contains a physician's full prescription for the usage of that device. As a result, the patient has practically no opportunity to use the device in any fashion other than in the manner prescribed by their physician.

The controlled protocol timer can include a refill mechanism. When less than a defined number of sessions remain, the medical device can inform the user via auditory, visual, or tactile signals. The device can provide instructions to contact the third party maintaining the device, optionally including a phone number. The device may also provide a unique code number to be provided to the third party. The third party inputs this unique code number into a software application along with the details of any desired changes to the profile. The software application then provides a new unique code number corresponding to the new profile. That new unique code number is then entered into the controlled protocol timer by the user, which decodes the new profile and allows for continued use of the device pursuant to the new profile.

The phototherapy device can also adjust its dosimetry. For example, it can measure the output of the ultraviolet lamp and adjust dosages to compensate for lamp aging, line voltage, and other variables known in the art.

The construction of the medical device is useful and provides user convenience and safety. For example, the device can monitor line voltage, current, frequency, phase, and power factor to provide for fault detection and diagnostics. It can accept input power from 90 VAC to 250 VAC, and 45 Hz to 65 Hz, providing efficient conversion with no need for user intervention. Line power can be magnetically coupled into the device via a transformer, reduced to low voltage within the power supply, and insulated from the user by having no conductive materials exposed. Devices having an access door have a door safety switch that detects the door opening, suspends treatment, and alerts the operator. A rechargeable energy source, a charger, and monitoring software may be included for use as backup power to ensure timekeeping and data retention functions. Triple-redundant safety protection can be provided by three independent shutoff mechanisms which guarantee that no exposure will be provided except as authorized by the prescription, even in the event of two credible simultaneous failures. Each shutoff mechanism can be independently verified before each treatment begins or on any other desired schedule.

Several user controls can be included for the patient to interact with the medical device. Audio controls may allow the volume of any audible alerts to be adjusted to suit the user and the ambient noise environment. Visual controls may be provided. For example, in some embodiments, the device can include six separate lights on a front panel. Two lights are hard-wired (power, lamp on) and four are controlled by firmware/software within the device to indicate various fault or alert conditions. The operator can adjust display brightness and contrast to suit his preferences. The device may use variable font sizes to indicate different information. For example, small fonts can be used for detailed diagnostic information and instructions, while larger fonts are used for visibility from greater distances for items such as the time-remaining countdown. Operator input can be accepted via sealed capacitive sensing "pushbuttons" located in such proximity to the display as to allow software-defined changes to the functionality of any given button by displaying appropriate nomenclature adjacent to the button. Other mechanical or other pushbutton technology may also be used. Low-noise capacitive touch detection may also be incorporated, where each keypad button serves as the timing capacitor for a simple and efficient relaxation oscillator. Multiple periods of this relaxation oscillator are timed, providing strong noise immunity. A baseline reference is maintained by the firmware to detect changes in capacitance when a key is touched, and debouncing is provided in firmware to prevent false touch detection.

As previously mentioned, the controlled protocol timer provides controls such that the user can only use the device in the manner prescribed by their physician. The medical device also provides controlled access to certain settings, such as through requiring authentication to view or adjust certain internal settings. This authentication can be provided using a simple passcode or using more sophisticated rolling-code or challenge-response type authentication mechanisms. The initial session time can also be preprogrammed at the factory prior to the medical device being delivered to the patient's home. This initial session time can then serve as the starting baseline point for all of the remaining sessions from that device. If desired, other external sensors can also be connected to the device, for example via the One-Wire™ bus promulgated by Dallas Semiconductor.

As previously discussed, the controlled prescription timer limited only the number of sessions allowed by the home phototherapy device. The controlled protocol timers of the present disclosure, on the other hand, include multiple control features. First, it counts and/or limits the number of allowed sessions to the number prescribed by the physician. Second it also limits the patient's usage to the frequency prescribed by the physician. For example, the controlled protocol timer can prevent the phototherapy device from operating any more frequently than a once-a-day or once-every-other-day regimen prescribed by the physician. Other intervals can be used as prescribed. Allowance can be made for slight variations in the patient's daily schedule by allowing a tolerance (such as 4%) in the minimum interval between sessions. Allowances can also be made for a weekly rotation for patient convenience, such as sessions on Monday, Wednesday, and Friday, rather than a fixed every-two-days interval. The controlled protocol timer can also limit the duration of each treatment to that prescribed by the physician.

The controlled protocol timers of the present disclosure are used to control a device, particularly a treatment dispensing device such as a phototherapy treatment dispensing device. The controlled protocol timer does this by containing the full prescription for the usage of the device. A first type of prescription might comprise a prescribed number of sessions, a prescribed session frequency, and a prescribed duration for each session. For example, a prescription might be for 10 sessions, one session per day, ten minutes per session. In some cases though, the prescription might call for a prescribed number of treatments per session. As one example, the prescribing physician may wish to treat the patient's front differently from the patient's back by exposing them to light for different periods of time. Then, this second type of prescription might comprise a prescribed number of sessions, a prescribed session frequency, a prescribed number of treatments per session, and a prescribed duration for each treatment. For example, such a prescription might be for 10 sessions, one session per day, two treatments per session, 10 minutes for the first treatment, 5 minutes for the second treatment. Of course, if the prescribed number of treatments per session is one, then the second type of prescription is the same as the first type of prescription.

The prescribed session frequency may vary between sessions. For example, a prescription for sessions on a Monday-Wednesday-Friday (M-W-F) schedule could be described as one day between M-W and W-F, then two days from Friday to Monday. The session frequency may also be described by multiple means. For example, the session frequency could be described as "one session per day," "at least 12 hours between sessions," or "only 10 minutes of light per 24 hour period." In other words, there is no one specific way to describe the session frequency.

In some embodiments, the controlled protocol timer takes the form of a controller configured to control the device, the controller including (A) an engine that contains a prescribed protocol, each protocol comprising (i) a prescribed number of sessions, (ii) a prescribed session frequency, (iii) a prescribed number of treatments per session, and (iv) a prescribed duration for each treatment.

The controller may further comprise (B) an input means for entering a passcode corresponding to a desired treatment schedule, wherein the engine further converts the passcode into a prescribed protocol. Exemplary input means include a display panel or control panel, a keyboard, a graphical display screen, and/or a touchscreen. These input means can use LED lights, graphical displays, keys or buttons, speakers, and other components to communicate information to the user. The input means can also allow for a prescription refill mechanism, as described further herein.

In particular embodiments, the treatment schedule is a prescription from a prescribing physician. The prescription can be converted as a prescribed protocol for the device to follow. The prescribed protocol may be expressed in different ways. For example, a protocol may comprise (i) a prescribed number of sessions, (ii) a prescribed session frequency, and (iii) a prescribed duration for each session. A protocol may also comprise (i) a prescribed number of sessions, (ii) a prescribed session frequency, (iii) a prescribed number of treatments per session, and (iv) a prescribed duration for each treatment. A protocol may also comprise a first session, a second session, and a session interval. In this last protocol, each session would have a duration and the session interval corresponds to a session frequency.

Besides the input means and the engine, the controlled protocol timer may further comprise (C) a treatment limiter configured to limit a number of treatments according to the prescribed number of sessions and the prescribed number of treatments per session of the protocol; (D) a frequency limiter configured to limit a frequency of sessions according to the prescribed session frequency of the protocol; and (E) a duration limiter configured to limit a duration of a particular treatment to the prescribed duration for that treatment according to the protocol. Depending on the protocol, the treatment limiter may essentially function as a session limiter as well. The treatment limiter, frequency limiter, and duration limiter can be three separate limiters or a single limiter that limits all three aspects (treatment number, frequency, and duration).

The controlled protocol timer of the present disclosure further includes at least one of the following three features: (1) the ability to control incremental exposure increases by the patient; (2) the ability to record patient usage of the device and form a treatment history; and (3) the ability to remind the patient of an overdue treatment. These features encourage compliance with the physician's prescription by controlling the usage of the phototherapy device, monitoring patient usage, and providing information that encourages patient compliance.

Figure 1:
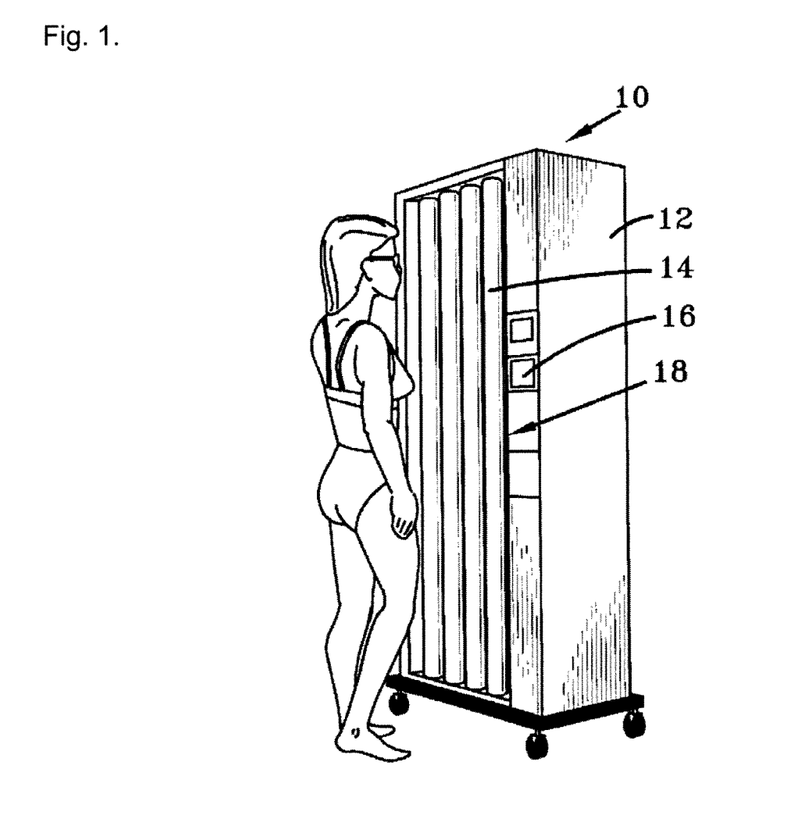
FIG. 1 is a perspective view of one embodiments of a phototherapy treatment dispensing device of the present disclosure.

Referring first to FIG. 1, an exemplary phototherapy treatment dispensing device 10 comprises an ultraviolet radiation reflecting panel 12 containing a bank of ultraviolet ray-emitting tubes 14. This device 10, by FDA regulations, can be sold only by the manufacturer to a patient upon presentation of a prescription from a duly accredited physician. The physician prescribes an initial treatment regimen comprising (i) a prescribed number of therapeutic light emissions treatments and (ii) a maximum duration of each treatment. The treatment regimen is converted by the controlled protocol timer into a prescribed protocol. A programmable controller 16 is mounted on the front face 18 of panel 12.

Figure 2:
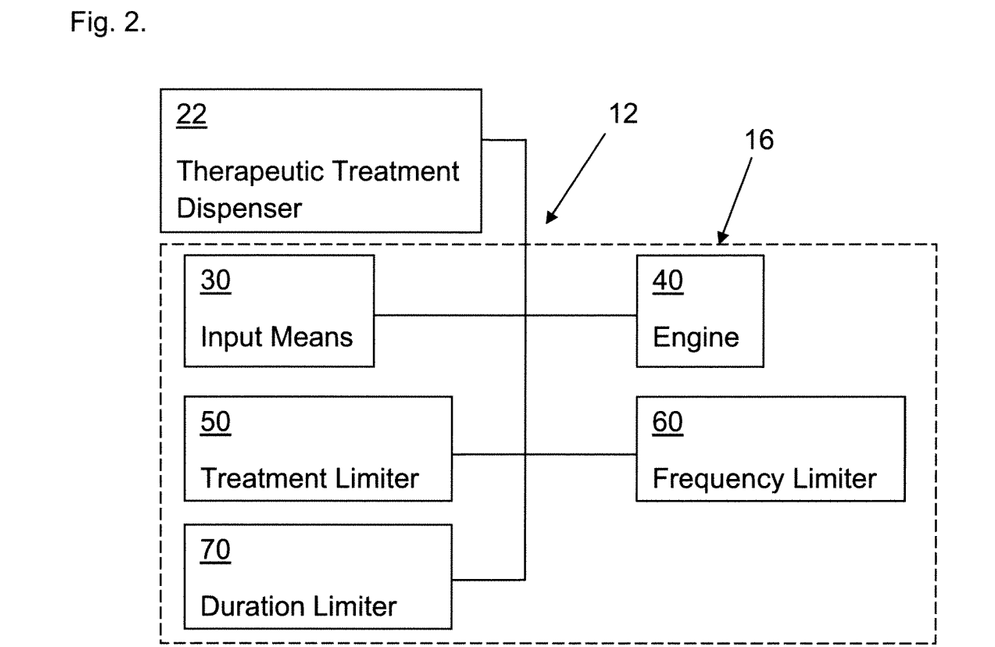
FIG. 2 is a block diagram of one embodiment of a treatment dispensing device of the present disclosure that dispenses treatments according to a prescribed protocol.

Referring to FIG. 2, a treatment dispensing device 12 comprises a therapeutic treatment dispenser 22 and a controller 16. The therapeutic treatment dispenser 22 dispenses a therapeutic treatment. An exemplary dispenser 22 is a generator 20, such as an ultraviolet radiation reflecting panel 12 containing a bank of ultraviolet ray-emitting tubes 14, as shown in FIG. 1. Other exemplary generators include those that can provide UVA light (320 nm to 400 nm), UVB light (280 nm to 320 nm), and blue light (400 nm to 495 nm).

The controller 16 includes an input means 30, an engine 40, a treatment limiter 50, a frequency limiter 60, and a duration limiter 70. The input means 30 allows a patient to enter a passcode corresponding to a particular prescription. The passcode may be formed from alphanumeric characters and be of any length necessary to fully describe the prescription, including from 4 to 16 characters. The engine 40 converts the passcode to a prescribed protocol, each protocol comprising (i) a prescribed number of sessions, (ii) a prescribed session frequency, (iii) a prescribed number of treatments per session, and (iv) a prescribed duration for each treatment. The treatment limiter 50 limits a number of therapeutic treatments according to the prescribed number of sessions and the prescribed number of treatments per session of the protocol. In other words, it counts the number of prescribed sessions or treatments and prevents the dispenser from activating once the protocol is complete. The frequency limiter 60 limits the frequency at which therapeutic treatments are dispensed according to the prescribed session frequency of the protocol. For example, if the protocol is for one session a day, then the frequency limiter prevents the dispenser for activating for the rest of the day after the patient has completed her session. The duration limiter 70 limits the duration of a particular treatment to the prescribed duration for the particular treatment according to the protocol. The three limiters 50, 60, 70 can be separate limiters or the same limiter can limit all three aspects (treatment number, frequency, and duration).

In a phototherapy device, the maximum duration of each therapeutic light emissions treatment is generally preset. The patient may generally adjust the duration downwards, i.e. to have a shorter duration. However, previous controlled prescription timers also permitted the patient to adjust the duration of the next treatment upwards. In some embodiments, the phototherapy treatment dispensing device provides a controlled protocol timer which controls incremental exposure increases by the patient.

Figure 3:
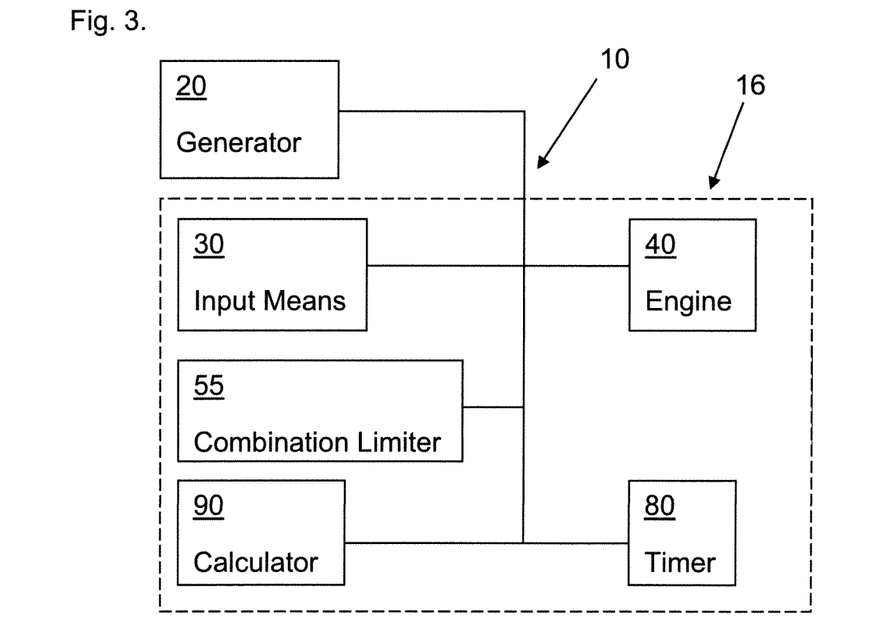
FIG. 3 is a block diagram of one embodiment of a phototherapy treatment dispensing device of the present disclosure that controls incremental exposure increases.

Referring to FIG. 3, the device 10 comprises a generator 20 and a controller 16. This controller, however contains combination limiter 55, which performs the same functions as treatment limiter 50, frequency limiter 60, and duration limiter 70. The controller 16 further comprises a timer 80 and a calculator 90. The timer 40 is used for timing at least (i) the actual duration of each therapeutic light emissions treatment and (ii) the total actual duration of therapeutic light emissions treatments in a first period of time.

The calculator 50 calculates the amount of incremental exposure increase which can be permitted. This incremental exposure increase can be done in one of two ways. First, the duration of treatments can be increased. In other words, the total duration of therapeutic light emissions treatments in a second period of time can be increased based on the total actual duration of therapeutic light emissions treatments in the first period of time. For example, a treatment of 1 hour in the first day might allow a treatment of 1.02 hours on the second day. Second, the session frequency can be decreased.

In other words, the session frequency can be decreased based on the total actual duration of therapeutic light emissions treatments in the first period of time. For example, where the prescription is 1 hour of treatment, wait 12 hours, then another 1 hours of treatment, the session frequency could be decreased to only waiting 11 hours.

The permitted increase in duration may be calculated in several ways. A first method of calculating the permitted increase may be based on a given percentage of the total duration of therapeutic light emissions treatments in the first period of time. The percentage may range, for example, from 2% to 4%. Thus, for example, a patient who had received light exposure for 1 hour on the first day would be allowed by the controlled protocol timer to self-adjust her light exposure to 1.02 hours on the second day. However, if the patient attempted to self-adjust her light exposure to 2 hours on the second day, the controlled protocol timer would either reject the patient's light exposure or automatically reduce it to 1.02 hours. This method can encourage patient compliance because the actual duration of a session or treatment is used to calculate the permitted increase, not the prescribed duration of the session or treatment. The percentage on which the permitted increase is based does not need to remain constant between sessions or treatments.

A second method of calculating the permitted increase may be based on the difference between the total actual duration of treatments in the first period of time and the prescribed duration of treatments for that first period of time. This method would allow a patient to "catch up" on the missing dosage. For example, a patient who had a prescription for 1 hour of light exposure a day, but who had only received 0.75 hours of light exposure on the first day, would be permitted by the controlled protocol timer to receive 1.25 hours of light exposure on the second day (0.25 hours catch-up time plus the prescribed 1.0 hour for the second day) or to receive the next scheduled session 0.25 hours earlier.

A third method of calculating the permitted increase may be based on a stepwise function determined by the total actual duration of treatments in the first period of time. This method would allow the physician to prevent incremental increases that may be inappropriate or unsafe at higher dosages. For example, a patient who had received light exposure of 1 to 2 hours in a day might be permitted to increase the duration of the next session by up to 15 minutes, but a patient who had received light exposure of 2 to 3 hours in a day might only be permitted to increase the duration of the next session by up to 5 minutes. Alternatively, the session frequency could be decreased so that a patient could receive the next session 15 minutes or 5 minutes earlier, respectively.

The first period of time and second period of time used by the calculator to calculate permitted increases do not need to be equal, though they generally are for purposes of convenience to the physician and patient. The length of each period of time may also vary. For example, the physician may wish to allow a patient to "catch up" on missing dosages, but only by a certain amount a day. Then, the first period of time might be longer than the second period of time. In particular embodiments, though, both periods of time are from about a day to about a week. They may also be from about a day to about three days. In other embodiments, the periods of time are both from 2 hours to 96 hours, from 12 hours to 48 hours, or about 24 hours. These periods are generally determined by how strictly the physician desires to control the patient's usage.

The engine 40, limiters 50, 60, 70, timer 80, and calculator 90 may generally be implemented as special firmware within the device or as software routines run by a controller 16 within the device. The input means 30 may be a separate physical component or be integrated with the controller 16.

Figure 4:
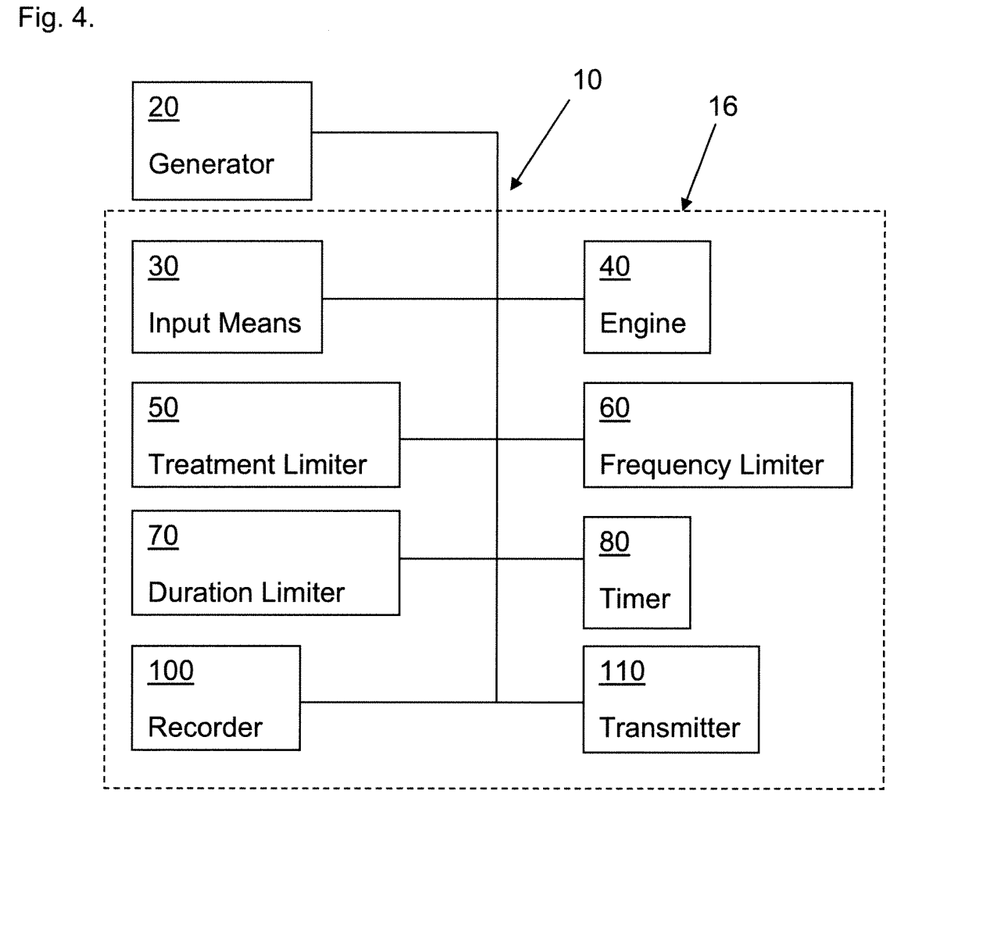
FIG. 4 is a block diagram of another embodiment of a phototherapy treatment dispensing device of the present disclosure that records patient usage of the device.

Other embodiments of the phototherapy treatment dispensing device provide the ability to record patient usage of the device and form a treatment history. Referring to FIG. 4, the device 10 comprises a generator 20 and a controller 16. Again, the controller comprises an input means 30, an engine 40, a treatment limiter 50, a frequency limiter 60, and a duration limiter 70 that function as described above. The controller also comprises a timer 80 that times at least (i) the actual duration of each therapeutic light emissions treatment and (iii) the time at which each therapeutic light emissions treatment begins. This information allows the patient's treatment history to be formed.

The device 10 further comprises a recorder 100 and a transmitter 110. The recorder 100 records the beginning time and the actual duration of each therapeutic light emissions treatment. The transmitter 110 can transmit the recorded beginning time and actual duration of each therapeutic light emissions treatment to a third party. Depending on the desires of the physician, the transmitter can be set to transmit (i) on a periodic basis (such as every week), (ii) after each treatment, (iii) after a set period of time, or (iv) after the entire protocol has been completed. Similarly, the recorder can record (i) only the last treatment, (ii) all treatments since last transmissions, or (iii) all treatments for the entire protocol. In other words, the recorder and transmitter can transmit the information for each treatment separately or record the information for multiple treatments and then transmit that accumulated information at one time. This can allow the physician to monitor the patient's compliance with the prescription or allow the patient to substantiate usage compliance of the phototherapy device to their medical insurance company.

The recorder can be implemented as a mechanical device, such as a paper printer or a tape cassette. However, the recorder is usually implemented as computer memory (flash, RAM, EPROM, etc.). The transmitter can be any item that successfully transmits information. Exemplary transmitters include a removable medium (such as a memory card), a wired connection (such as a serial connection or a modem connection), a wireless connection utilizing a sound, ultrasound, radio, microwave, infrared, or optical transmission medium, or a human-readable display that requires an authentication code. The connections generally allow the information to be transmitted over the Internet (or other proprietary networks); the provider of the connection (e.g. cable, DSL, satellite) is immaterial. The recorder and transmitter may also be embodied in the same device. For example, a removable memory card may simultaneously serve as the recorder and the transmitter. The recorder and transmitter may either be independent components of the device or be integrated with the controller 16.

Figure 5:
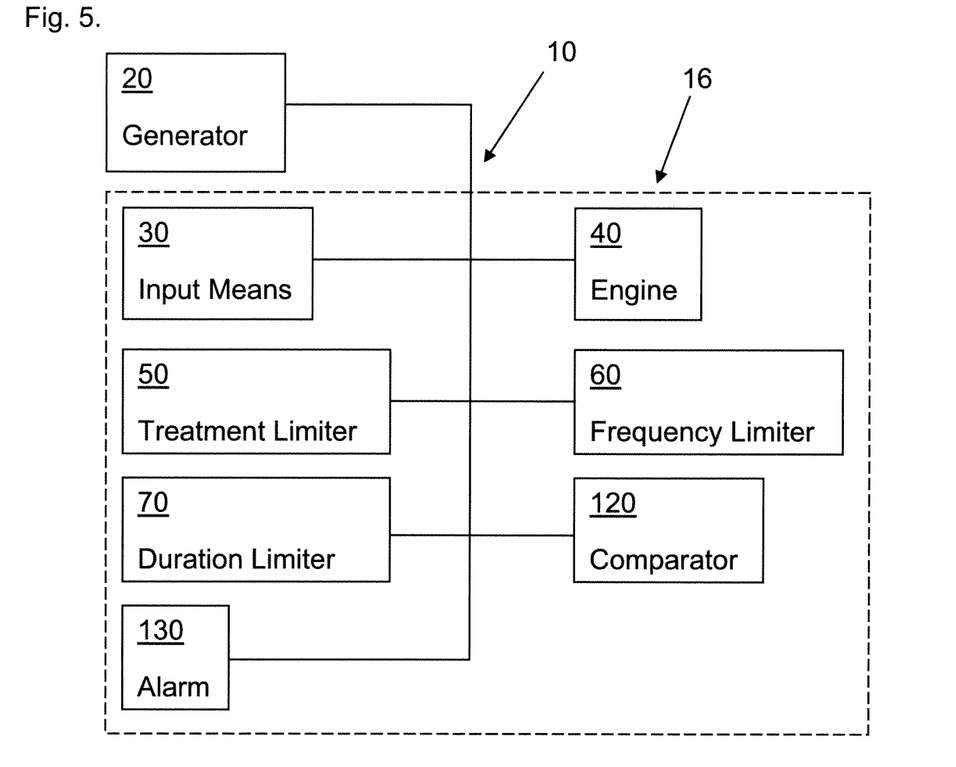
FIG. 5 is a block diagram of another embodiment of a phototherapy treatment dispensing device of the present disclosure that reminds the patient of an overdue treatment.

Other embodiments of the phototherapy treatment dispensing device provide the ability to remind the patient of an overdue treatment. Referring to FIG. 5, the device 10 comprises a generator 20 and a controller 16. The controller includes an input means 30, an engine 40, a treatment limiter 50, a frequency limiter 60, and a duration limiter 70 that function as described above. In these embodiments, the session frequency of the prescription is easier visualized as a session interval, or an interval between sessions.

The device 10 further comprises a comparator 120 and an alarm 130. The comparator compares (iv) an elapsed time beginning after the end of a session. The comparator 90 compares the elapsed time to the prescribed session frequency (or session interval). When the elapsed time differs from the prescribed session frequency by a specified amount, the alarm 100 generates an alert.

The specified amount may be considered as a percentage of the prescribed session frequency, a fixed amount, a stepwise function, or inversely related to the prescribed session frequency. In other words, the specified amount may vary between sessions and does not need to be fixed. It may vary, for instance, depending on how the patient uses the machine. For example, the protocol calls for a one session of 10 minutes each day. Here, the prescribed session frequency is expressed as one session a day. If the patient takes the first session at 10:00 pm on day 1, then the device might wait until 11:30 pm on day 2, or an interval of 25 hours 30 minutes, before alerting the patient, who can then meet the protocol (and their prescription) by beginning her 10 minute session for day 2 within the next 20 minutes. Then the device might wait again until 11:30 pm on day 3, or an interval of 23 hours 30 minutes, before alerting the patient again. In these embodiments, the alarm generally generates an alert prior to the patient missing a session. If the alarm is generated prior to the patient missing a session, the specified amount should be considered as a positive value. If the alarm is generated after the session frequency has elapsed, the specified amount should be considered as a negative value. As an example of a fixed specified amount, the device might always alert the patient one hour before the session frequency will elapse.

The comparator 120 may be special firmware within the device or a software routine run by a microprocessor within the device. The comparator may also contain its own clock that allows it to measure the elapsed time, rather than needing a separate timer (though one can be provided). The alarm 130 may be auditory (such as a siren), visual (via graphical display screen, light, LED), or tactile. The alarm may also be a separate physical component or be integrated with the controller 16.

Figure 6:
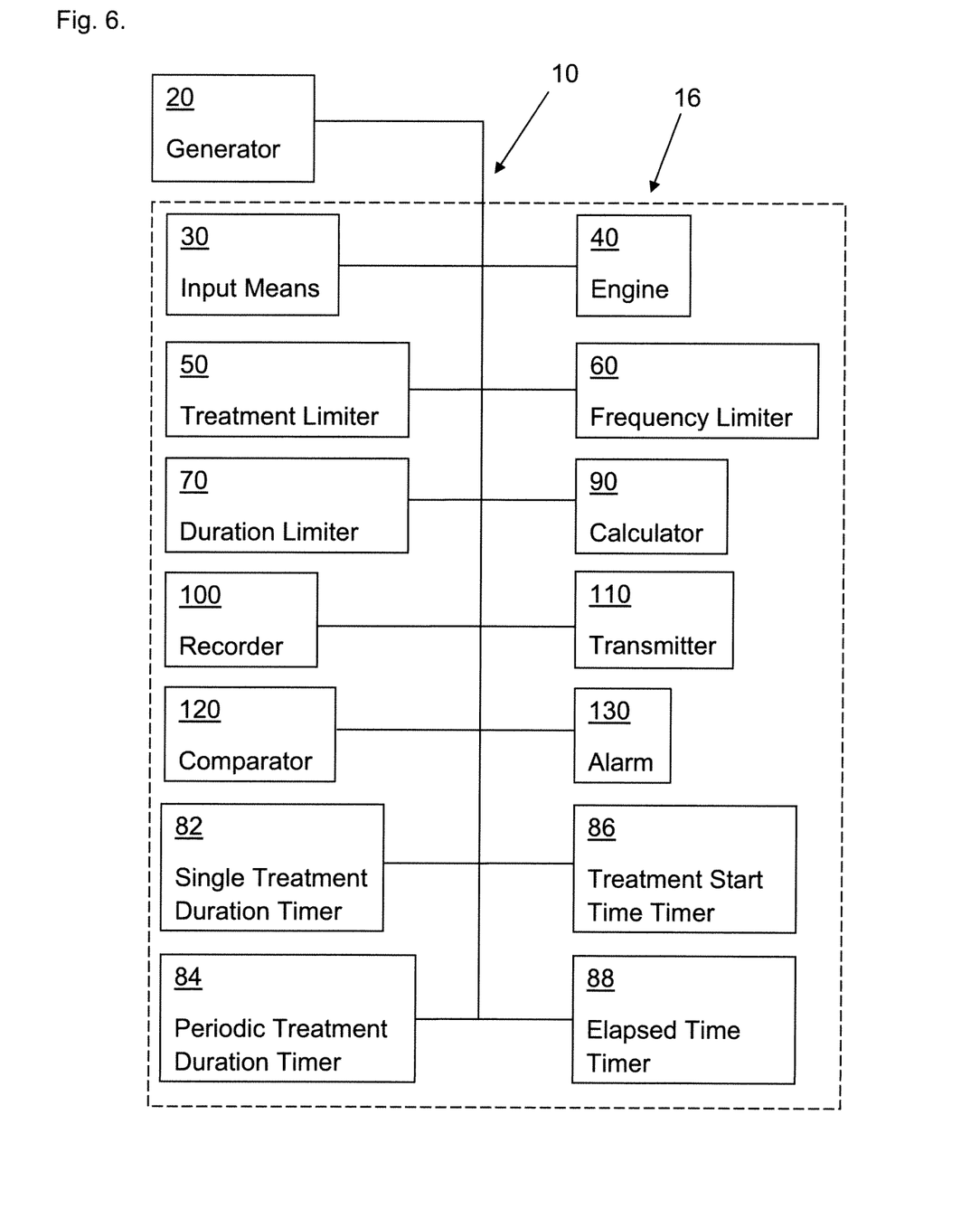
FIG. 6 is a block diagram of another embodiment of a phototherapy treatment dispensing device of the present disclosure that has multiple control features.

The phototherapy devices of the present disclosure can also include the components necessary to achieve any combination of the three features. For example, referring to FIG. 6, the device 10 can comprise a generator 20, an input means 30, an engine 40, a treatment limiter 50, a frequency limiter 60, a duration limiter 70, multiple timers 82, 84, 86, 88, a calculator 90, a recorder 100, a transmitter 110, a comparator 120, an alarm 130 for providing all three features in the same device. More than one timer may be present. For example, there may be four timers, one each for timing (i) the actual duration of a therapeutic light emissions treatment 82; (ii) the total duration of therapeutic light emissions treatments in a period of time 84; (iii) the beginning time of a therapeutic light emissions treatment 86; and (iv) the elapsed time since the end of a therapeutic light emissions treatment 88. These devices allow the patient's exposure to be controlled.

It should be understood that in the preceding description, the term "device" refers to a phototherapy device that includes the controlled protocol timer for controlling the on/off function of the generator. In other words, the term "controlled protocol timer" can refer to the logical components of the phototherapy device or a single physical component of the phototherapy device. For example, the controlled protocol timer can, if desired, be implemented as a microprocessor 22 which runs functions corresponding to the engine 40, a treatment limiter 50, a frequency limiter 60, a duration limiter 70, timer 80, calculator 90, recorder 100, transmitter 110, and comparator 120. The phototherapy device may also include an input means 30, recorder 100, a transmitter 110, and/or an alarm 130 as physical components separate from the microprocessor.

Figure 7:
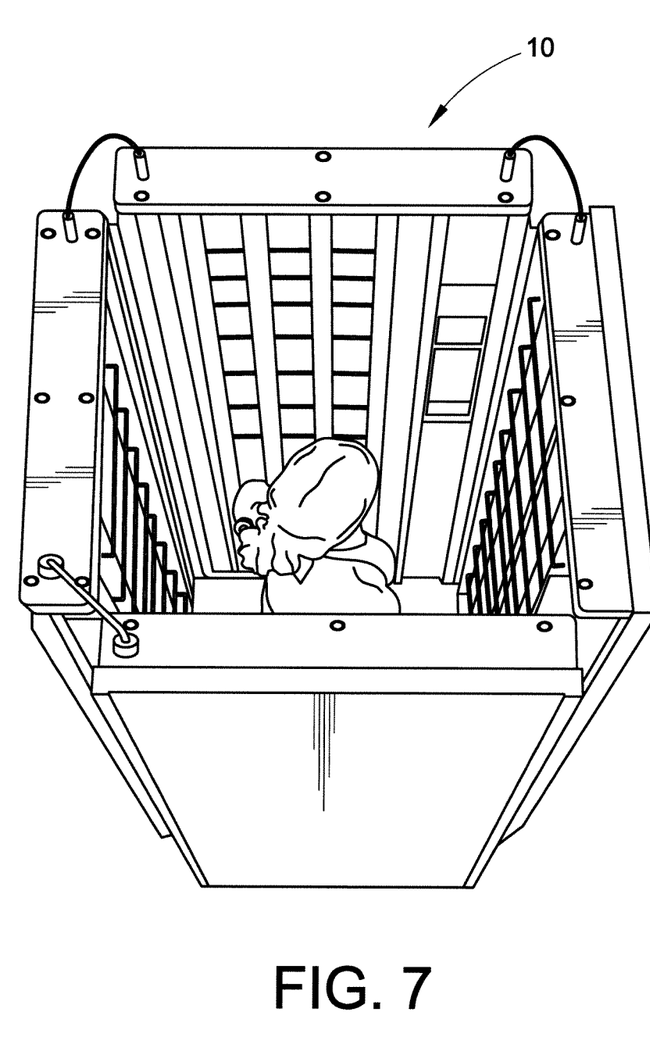
FIG. 7 is a perspective view of an exemplary booth form of the phototherapy treatment dispensing device of the present disclosure.
Figure 8:
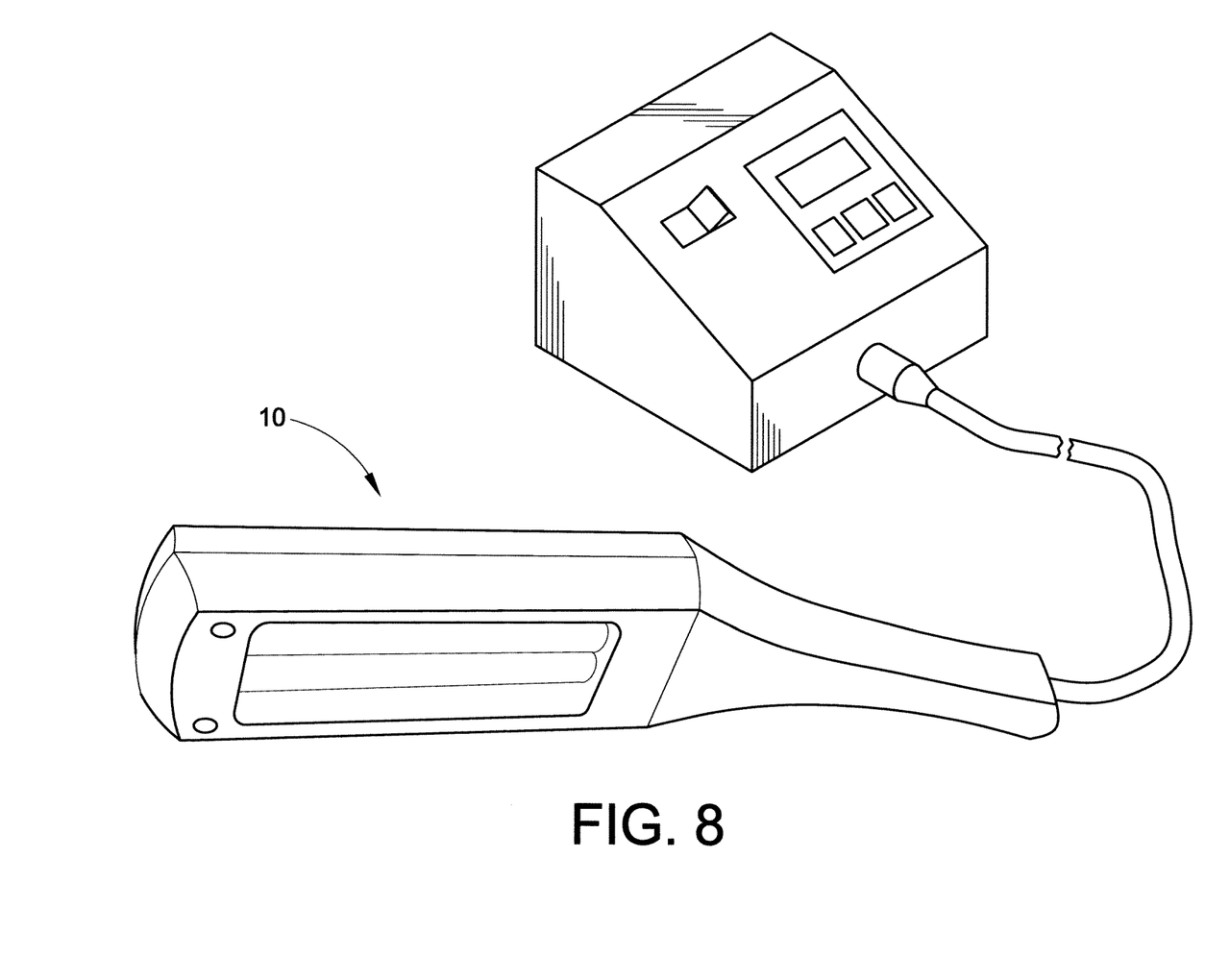
FIG. 8 is a perspective view of an exemplary handheld wand form of the phototherapy treatment dispensing device of the present disclosure.
Figure 9:
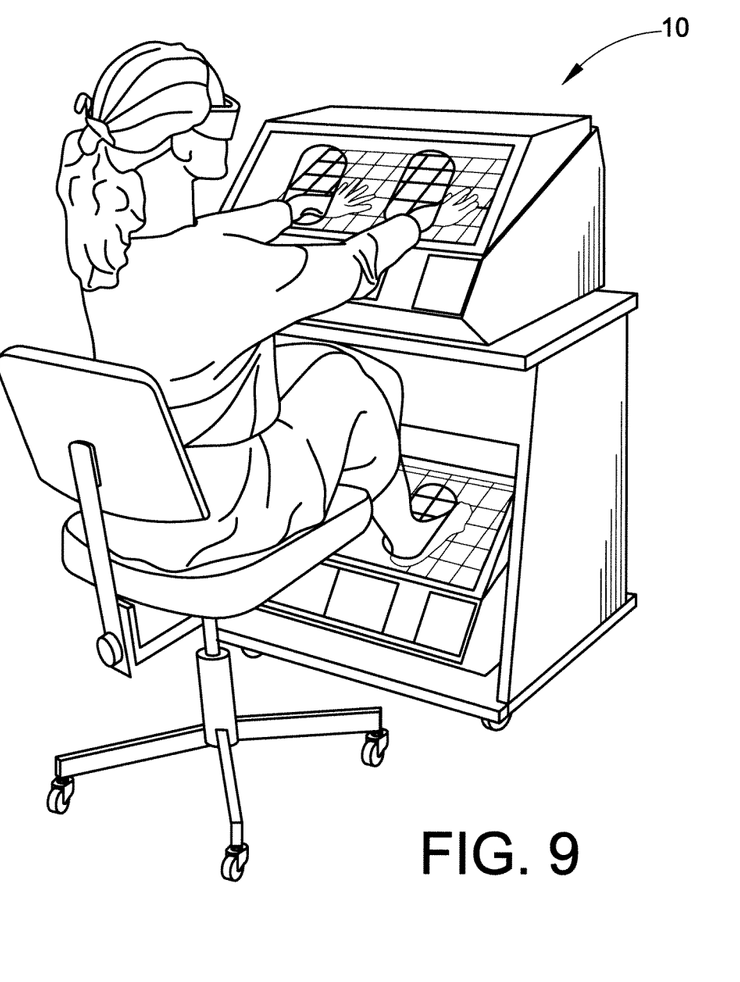
FIG. 9 is a perspective view of an exemplary desk-type device form of the phototherapy treatment dispensing device of the present disclosure.

The phototherapy treatment dispensing device 10 depicted herein is a 6-foot tall panel. However, the device is not restricted only to such panels. For example, the device could be in the form of a tanning bed or a booth that surrounds the patient. The device could also be a 2-foot panel, a handheld wand, or a desk-type device for the treatment of hands and/or feet. An exemplary booth is shown in FIG. 7; an exemplary handheld wand is shown in FIG. 8; and an exemplary desk-type device is shown in FIG. 9 for both hands and feet. The panels making up the booth of FIG. 7 can also be foldable for a smaller footprint during storage if desired.

Persons having ordinary skill in the art will be able to make the embodiments described above or combinations of the embodiments described above using methods known in the art.

Various methods for controlling the usage of a treatment dispensing device and controlling the exposure of a patient using a light treatment dispensing device are also provided. The methods all require that the device be capable of producing a treatment and providing a prescribed protocol using the controlled protocol timer. In some methods, the production of treatments is limited based on the prescribed protocol. In other methods, the beginning time and duration of the light treatments are recorded and transmitted to a third party. Such information for multiple treatments can be recorded and then transmitted simultaneously. In still other methods, an alarm is generated if an elapsed time between sessions exceeds the session interval by a specified amount.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A light treatment dispensing device comprising:
   a generator including a light emission device for emitting a therapeutic light emissions treatment; and
   a controller configured to control the generator, the controller including:
   (A) an engine that is configured to determine a prescribed protocol based on an input to the controller, the prescribed protocol comprising (i) a prescribed number of sessions, (ii) a prescribed session frequency, (iii) a prescribed number of treatments per session, and (iv) a prescribed duration for each treatment
   (B) a treatment limiter configured to limit a number of therapeutic light emissions treatments according to the prescribed number of sessions and the prescribed number of treatments per session of the protocol;
   (C) a frequency limiter configured to limit a frequency at which therapeutic light emissions treatments are dispensed according to the prescribed session frequency of the protocol;
   (D) a duration limiter configured to limit a duration of a particular treatment to the prescribed duration for the particular treatment according to the protocol; and
   a timer configured to time a total actual duration of therapeutic light emissions treatments in a first period of time.

2. The device of claim 1, wherein the input to the controller is a passcode and the controller further includes an input means for entering the passcode corresponding to a desired prescription, wherein the engine is configured to convert the passcode to the prescribed protocol.

3. The device of claim 1, wherein the timer further times an actual duration and a beginning time of a therapeutic light emissions treatment; and
   the device further comprises a recorder for recording the beginning time and the actual duration of the therapeutic light emissions treatment.

4. The device of claim 3, further comprising:
   a transmitter for transmitting the recorded beginning time and actual duration of the therapeutic light emissions treatment to a third party.

5. The device of claim 1, further comprising:
   a comparator for comparing (i) an elapsed time beginning after the end of a particular session and (ii) the prescribed session frequency; and
   an alarm for generating an alert when the elapsed time differs from the prescribed session frequency by a specified amount.

6. The device of claim 1, further comprising:
   a calculator for calculating a permitted increase in a total duration of therapeutic light emissions treatments in a second period of time based on the total actual duration of therapeutic light emissions treatments in the first period of time.

7. The device of claim 6 wherein the permitted increase is based on a percentage of the total actual duration of therapeutic light emissions treatments in the first period of time.

8. The device of claim 6 wherein the first and second periods of time are both from 2 hours to 96 hours.

9. A light treatment dispensing device comprising:
   a generator including a light emission device for emitting a therapeutic light emissions treatment; and
   a controller configured to control the generator, the controller including:
      (A) an engine that is configured to determine a prescribed protocol based on an input to the controller, the prescribed protocol comprising (i) a prescribed number of sessions, (ii) a prescribed session frequency, (iii) a prescribed number of treatments per session, and (iv) a prescribed duration for each treatment;
      (B) a limiter configured to limit (i) a number of therapeutic light emissions treatments according to the prescribed number of sessions and the prescribed number of treatments per session of the protocol, (ii) a frequency at which therapeutic light emissions treatments are dispensed according to the prescribed session frequency of the protocol, and (iii) a duration of a particular treatment to the prescribed duration for the particular treatment according to the protocol; and
      (C) a timer configured to time a total actual duration of therapeutic light emissions treatments in a first period of time.

10. The device of claim 9, wherein the input to the controller is a passcode and the controller further includes an input means for entering the passcode corresponding to a desired treatment schedule, wherein the engine is configured to convert the passcode to the prescribed protocol.

11. The device of claim 9, further comprising:
    a calculator for calculating a permitted decrease in a session frequency based on the total actual duration of therapeutic light emissions treatments in the first period of time.

12. A phototherapy treatment dispensing device comprising:
    a generator for generating a therapeutic light emissions treatment;
    a controller configured to control the generator, the controller including:
       (A) an engine that is configured to determine a prescribed protocol based on an input to the controller, the prescribed protocol comprising (i) a prescribed number of sessions, (ii) a prescribed session frequency, (iii) a prescribed number of treatments per session, and (iv) a prescribed duration for each treatment;
       (B) a treatment limiter configured to limit a number of therapeutic light emissions treatments according to the prescribed number of sessions and the prescribed number of treatments per session of the protocol;
       (C) a frequency limiter configured to limit a frequency at which therapeutic light emissions treatments are dispensed according to the prescribed session frequency of the protocol;
       (D) a duration limiter configured to limit a duration of a particular treatment to the prescribed duration for the particular treatment according to the protocol; and
       (E) a timer for timing an actual duration of the therapeutic light emissions treatment and a beginning time of the therapeutic light emissions treatment;
    a recorder for recording the beginning time and the actual duration of the therapeutic light emissions treatment; and
    a transmitter for transmitting the recorded beginning time and actual duration of the therapeutic light emissions treatment to a third party.

13. The device of claim 12, wherein the input to the controller is a passcode and the controller further includes an input means for entering the passcode corresponding to a desired treatment schedule, wherein the engine is configured to convert the passcode to the prescribed protocol.

14. The device of claim 12, wherein the transmitter is selected from the group consisting of a removable medium, a wired connection, a wireless connection utilizing a sound, ultrasound, radio, microwave, infrared, or optical transmission medium, or a human-readable display that requires an authentication code.

15. The device of claim 12, wherein the timer further times a total actual duration of therapeutic light emissions treatments in a first period of time; and
    the device further comprises a calculator for calculating a permitted increase in the total duration of therapeutic light emissions treatments in a second period of time based on the total actual duration of therapeutic light emissions treatments in the first period of time.

16. The device of claim 12, further comprising:
    a comparator for comparing (i) an elapsed time beginning after the end of a particular session and (ii) the prescribed session frequency; and
    an alarm for generating an alert when the elapsed time differs from the prescribed session frequency by a specified amount.

17. A phototherapy treatment dispensing device for providing a therapeutic radiation treatment, the device including a controller configured to perform a method comprising:
    providing a prescribed protocol, the protocol based on an input to the controller, the prescribed protocol comprising (i) a prescribed number of sessions, (ii) a prescribed session frequency, (iii) a prescribed number of treatments per session, and (iv) a prescribed duration for each treatment;
    timing an elapsed time beginning after the end of a particular session;

comparing the elapsed time to the prescribed session frequency; and generating an alert when the elapsed time differs from the prescribed session frequency by a specified amount.

18. The device of claim 17, wherein the specified amount is a percentage of the prescribed session frequency.

19. A treatment dispensing device comprising:
a treatment dispenser; and
a controller, the controller including:
(A) an engine that is configured to determine a prescribed protocol based on an input to the controller, the prescribed protocol comprising (i) a prescribed number of sessions, (ii) a prescribed session frequency, (iii) a prescribed number of treatments per session, and (iv) a prescribed duration for each treatment;
(B) a treatment limiter configured to limit a number of dispensed treatments according to the prescribed number of sessions and the prescribed number of treatments per session of the protocol;
(C) a frequency limiter configured to limit a frequency at which treatments are dispensed according to the prescribed session frequency of the protocol; and
(D) a duration limiter configured to limit a duration of a particular treatment to the prescribed duration for the particular treatment according to the protocol.

20. The device of claim 19, wherein the input to the controller is a passcode and the controller further includes an input means for entering the passcode corresponding to a desired treatment schedule, wherein the engine is configured to convert the passcode to the prescribed protocol.

21. A method for controlling the exposure of a patient using a light treatment dispensing device, comprising:
providing a light treatment device capable of producing a therapeutic light emissions treatment and containing a prescribed protocol based on an input to the controller, the prescribed protocol comprising (i) a prescribed number of sessions, (ii) a prescribed session frequency, (iii) a prescribed number of treatments per session, and (iv) a prescribed duration for each treatment;
producing a therapeutic light emissions treatment;
recording a beginning time and an actual duration of the therapeutic light emissions treatment; and
transmitting the recorded beginning time and actual duration of the therapeutic light emissions treatment to a third party.

22. The method of claim 21, wherein multiple therapeutic light emissions treatments are produced; the beginning time and actual duration of each treatment is recorded, and the recorded beginning time and actual duration of the multiple treatments are simultaneously transmitted to the third party.

23. A method for controlling the exposure of a patient using a phototherapy treatment dispensing device, comprising:
providing a phototherapy treatment device capable of (A) producing a therapeutic light emissions treatment and (B) containing a prescribed protocol, each protocol comprising a first session, a second session, and a session interval;
comparing (i) an elapsed time beginning after the end of the first session and (ii) the session interval; and
generating an alarm when the elapsed time differs from the session interval by a specified amount.

24. A method for controlling the usage of a treatment dispensing device, comprising:
entering a passcode corresponding to a particular profile;
providing a treatment device capable of dispensing a treatment and generating a prescribed protocol from the passcode, each prescribed protocol comprising (i) a prescribed number of sessions, (ii) a prescribed session frequency, and (iii) a prescribed duration for each session;
limiting the number of sessions to the prescribed number of sessions of the protocol;
limiting the frequency between successive sessions to the prescribed session frequency of the protocol; and
limiting the duration of a particular session to the prescribed duration for the particular session according to the protocol.

25. The method of claim 24, further comprising:
measuring a total actual duration of treatments dispensed in a first period of time; and
determining a permitted increase in a total duration of treatments allowed in a second period of time based on the total actual duration of treatments dispensed in the first period of time.

26. The method of claim 24, further comprising:
recording a beginning time and an actual duration of each treatment; and
transmitting the recorded beginning time and actual duration of each treatment to a third party.

27. The method of claim 24, further comprising:
recording the ending time of a treatment and an elapsed time since the ending time; and
generating an alarm when the elapsed time differs from the prescribed session frequency of the protocol.

* * * * *